(12) United States Patent
Gagnon

(10) Patent No.: US 9,988,418 B2
(45) Date of Patent: *Jun. 5, 2018

(54) METHODS FOR REDUCING AGGREGATE LEVELS IN PROTEIN PREPARATIONS BY TREATMENT WITH THIO-HETEROCYCLIC CATIONS

(71) Applicant: AGENCY FOR SCIENCE, TECHNOLOGY AND RESEARCH, Connexis (SG)

(72) Inventor: Peter Stanley Gagnon, Centros (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 241 days.

This patent is subject to a terminal disclaimer.

(21) Appl. No.: 14/766,123

(22) PCT Filed: Feb. 5, 2014

(86) PCT No.: PCT/SG2014/000048

§ 371 (c)(1),
(2) Date: Aug. 5, 2015

(87) PCT Pub. No.: WO2014/123486

PCT Pub. Date: Aug. 14, 2014

(65) Prior Publication Data

US 2015/0376230 A1   Dec. 31, 2015

Related U.S. Application Data

(60) Provisional application No. 61/761,646, filed on Feb. 6, 2013.

(51) Int. Cl.
| | | |
|---|---|---|
| *C07K 1/14* | (2006.01) | |
| *C07K 16/00* | (2006.01) | |
| *B01D 15/36* | (2006.01) | |
| *C07K 1/16* | (2006.01) | |
| *B01D 15/34* | (2006.01) | |
| *C07K 1/20* | (2006.01) | |
| *C07K 16/30* | (2006.01) | |
| *B01D 15/32* | (2006.01) | |
| *B01D 15/38* | (2006.01) | |

(52) U.S. Cl.
CPC .............. *C07K 1/14* (2013.01); *B01D 15/34* (2013.01); *B01D 15/363* (2013.01); *C07K 1/165* (2013.01); *C07K 1/20* (2013.01); *C07K 16/00* (2013.01); *C07K 16/3015* (2013.01); *B01D 15/327* (2013.01); *B01D 15/3828* (2013.01)

(58) Field of Classification Search
None
See application file for complete search history.

(56) References Cited

U.S. PATENT DOCUMENTS

| 5,283,339 | A | 2/1994 | Arnold et al. |
| 5,883,256 | A * | 3/1999 | Schuler ................. A61L 2/0088 |
| | | | 544/37 |
| 7,176,308 | B2 | 2/2007 | Vig et al. |
| 2009/0143529 | A1 | 6/2009 | Hearn et al. |
| 2009/0306342 | A1 | 12/2009 | Maeji et al. |
| 2009/0318674 | A1 | 12/2009 | Gagnon |
| 2013/0338344 | A1 * | 12/2013 | Ramasubramanyan |
| | | | ............................. C07K 1/165 |
| | | | 530/389.2 |
| 2014/0179008 | A1 * | 6/2014 | Lin ........................ G01N 30/34 |
| | | | 436/18 |

FOREIGN PATENT DOCUMENTS

| JP | S55-15444 | 2/1980 |
| JP | 2004-532262 | 10/2004 |
| WO | WO 2011/140406 | 11/2011 |
| WO | WO 2013/180648 | 12/2013 |
| WO | WO 2013/180655 | 12/2013 |
| WO | WO2012/169970 | 12/2015 |

OTHER PUBLICATIONS

Mark Wainwright "Photodynamic antimicrobial chemotherpay (PACT)" J. Antimicrobial Chemotherapy 42, 13-28, 1998.*
Extended European Search Report dated Sep. 20, 2016 for Appln. No. 14748942.1.
Riggert et al., "Filtration of methylene blue-photooxidized plasma: influence on coagulation and cellular contamination", Transfusion, vol. 41, Jan. 2001, pp. 82-86.
Legallais et al., "Strategies for the depyrogenation of contaminated immunoglobulin G solutions by histidine-immobilized hollow fiber membrane", Journal of Chromatography B., 1997, vol. 691, pp. 33-41.
"Protein Purification Profinity Tm IMAC Resins", Bio-Rad Laboratories Inc., Bulletin No. 3193., PDF document created 2005. Retrieved online Mar. 28, 2014 from http://www.bio-rad.com/webroot/web/pdf/lsr/literature_/Bulletin_3193.pdf.
"Chelex 100 and Chelex 20 Chelating Ion Exchange Resin Instruction Manual", Bio-Rad Laboratories Inc., Bulletin No. LIT2000. PDF document created 1998, Retrieved online Mar. 28, 2014 from http://www.bio-rad.com/webroot/web/pdf/lsr/liturature/LIT200.pdf.
International Search Report dated Apr. 4, 2014 for PCT/SG2014/000046.
International Search Report dated Mar. 31, 2014 for PCT/SG2014/000048.
International Preliminary Report of Patentability dated Aug. 11, 2015 for Appl. No. PCT/SG2014/000046.

(Continued)

*Primary Examiner* — Daniel E Kolker
*Assistant Examiner* — James L Rogers
(74) *Attorney, Agent, or Firm* — Pillsbury Winthrop Shaw Pittman LLP

(57) ABSTRACT

A method of reducing the aggregate content in a protein preparation having a target protein includes contacting the protein preparation with a thio-heterocyclic cation to form a mixture, contacting the mixture with at least one functionalized solid to remove excess thio-heterocyclic cations; and optionally contacting the mixture, simultaneously or sequentially, with at least one further functionalized solid to further reduce aggregate content of the protein preparation.

16 Claims, No Drawings

(56) References Cited

OTHER PUBLICATIONS

Gan et al., "Characterization and removal of aggregates formed by nonspecific interaction of IgM monoclonal antibodies with chromatin catabolites during cell culture production", Journal of Chromatography A 1291, (2013), pp. 33-40.
Official Action dated Aug. 29, 2017, for related Japanese Patent Application No. 201-555969. (English translation only).
Written Opinion dated Oct. 11, 2017, for related Singapore Patent Application No. 11201505195ST.
Shojania, A. Majid, et al., "The effect of Toluidine blue and methlene blue in immunochemical reactions in vitro," Clinical Immunology and Immunopathy, 1987, vol. 43, No. 2, pp. 223-228. (In Japanese and English).
Journal of the Japan Society of Blood Transfusion, 2005, vol. 51, No. 5, pp. 491-506. (In Japanese and English).

* cited by examiner

METHODS FOR REDUCING AGGREGATE LEVELS IN PROTEIN PREPARATIONS BY TREATMENT WITH THIO-HETEROCYCLIC CATIONS

STATEMENT OF RELATED APPLICATIONS

This application claims priority U.S. 61/761,646, filed Feb. 6, 2013, the entirety of which is incorporated herein by reference.

BACKGROUND

Embodiments disclosed herein relate to methods for enhancing purification of proteins, including antibodies. In particular, embodiments relate to methods for reducing the level of aggregates. Such methods may be performed in conjunction (sequentially or simultaneously) with clarification of cell culture harvest. Embodiments disclosed herein further relate to integration of these capabilities with other purification methods to achieve the desired level of final protein purity.

Aggregate removal has recognized value in protein purification. It has been shown that low concentrations of the yellow fluorescent heterocyclic dye ethacridine reduced aggregate content of antibody preparations (Gan et al J. Chromatography A 1291 (2013) 33-40). Ethacridine is used as a precipitating agent in the field of protein purification.

The thio-heterocyclic cation methylene blue is used to inactivate virus of therapeutic protein preparations produced by fractionation of blood plasma. It is also used as an anti-malarial drug and for treatment of methemoglobinemia and certain cancers.

SUMMARY

In some aspects, embodiments disclosed herein provide methods of reducing the aggregate content in a protein preparation comprising a target protein, the methods comprising contacting the protein preparation with a thio-heterocyclic cation to form a mixture, contacting the mixture with at least one functionalized solid to remove excess thio-heterocyclic cations, and optionally contacting the mixture, simultaneously or sequentially, with at least one further functionalized solid to further reduce aggregate content of the protein preparation.

DETAILED DESCRIPTION

Methods and kits are provided for the purification of proteins. In certain embodiments the disclosed methods provide for the reduction of aggregates from preparations of antibodies or other proteins through the contact of such desired proteins with one or more thio-heterocyclic cations. In certain embodiments, the disclosed methods may be practiced at a range of conductivity levels from so-called physiological conditions (about 12 to about 16 mS/cm) to conductivity values up to three or more times higher than such conditions. Such elevated conductivity levels may permit the methods to be applied to acidic proteins without risking their precipitation during treatment, and thereby increase the diversity of desired protein species to which the disclosed methods may be applied. In certain embodiments, the disclosed methods may be practiced with ultralow concentrations of the thio-heterocyclic cations; such as from about 0.01% to about 0.05%. The disclosed methods comprise contacting the treated protein preparation with solid materials that enhance the overall ability of the treatment to reduce aggregate content, usually in parallel with reducing host protein contamination, and provide the additional advantage of removing excess thio-heterocyclic cations. In certain embodiments, the thio-heterocyclic cation is methylene blue.

In certain embodiments, the disclosed methods provide for reducing levels of aggregates which have high molecular weight in comparison with the desired protein, such as homo-aggregates, consisting of multiples of the desired protein or multiples of another single-species, and hetero-aggregates, consisting of one or more of the desired protein combined with at least one other species or combinations of species lacking the desired protein. In certain embodiments, aggregates comprise hetero-aggregates of the desired protein and a contaminant and in certain such embodiments the contaminant is a nucleic acid, nucleotide, endotoxin, metal ion, protein, lipid, or cell culture media component. In certain embodiments, the presence of homo-aggregates of the desired protein is substantially eliminated. In certain embodiments, the presence of hetero-aggregates of the desired protein and a contaminant is substantially eliminated. In certain embodiments, the presence of homo- and hetero-aggregates not including the desired protein are substantially eliminated.

In certain embodiments, the disclosed methods additionally provide for the reduction of contaminants such as DNA, endotoxin, and virus levels along with reduction of aggregates. In certain embodiments the disclosed methods is practiced with the additional inclusion of antiviral agents beyond the thio-heterocyclic cation itself.

In certain embodiments, the protein species of interest (e.g., the desired protein to be purified) is of recombinant origin, and the protein preparation may include a cell-containing cell culture harvest, a cell culture supernatant, clarified cell culture supernatant, an eluate from a chromatography column, or protein-containing solution obtained from a previous stage of purification. In certain embodiments, the protein preparation contains an antibody and in certain of such embodiments the antibody is an IgG, an IgM, or a fragmentary form thereof, or a fusion protein of an antibody or antibody fragment, such as an Fc-fusion protein. In certain embodiments, the desired protein may be a clotting protein, such as Factor VIII. In certain embodiments, the desired protein may be a peptide hormone, such as human growth hormone.

In certain embodiments, the disclosed methods may be practiced such that the conductivity of the sample is at a sufficiently high level to substantially avoid precipitation of the desired protein from the sample. Conductivity may be adjusted by addition of salts or diluents according to methods known in the art. In certain embodiments, the conductivity is about 5 mS/cm, about 10 mS/cm, about 15 mS/cm or about 20 mS/cm greater than the level determined to be needed to avoid substantial precipitation of the desired protein. In certain embodiments, the conductivity is greater than about 20 mS/cm, about 25 mS/cm, about 30 mS/cm, about 35 mS/cm, about 40 mS/cm, about 45 ms/cm or greater than about 45 mS/cm. The ability of the methods to remove certain subsets of contaminants at elevated conductivities represents one of the surprising features of the disclosed methods, since charge interactions in these system are known to be reduced at elevated conductivities. At conductivities of about 25 mS/cm and higher; for example, only a minority of negatively charged proteins are known to bind to electropositive surfaces. Apart from the present methods, application of many electropositive agents to preparations of IgG antibodies occurs at conductivities less than about 5 mS/cm, and usually with the additional operating requirement of alkaline pH. Such an operating pH is not a requirement of the present methods. It will be apparent to the person of ordinary skill in the art that elevated conductivity may have the effect of weakening internal electrostatic associations within aggregates and thereby increase the ability of the method to achieve dissociation of aggregates and/or removal of contaminants associated with the desired protein.

In certain embodiments, the thio-heterocyclic cation is methylene blue (IUPAC name: [7-(dimethylamino)phenothiazin-3-ylidene]-dimethylazanium, an analogue, or a salt thereof. Analogues of methylene blue may also serve as the thio-heterocyclic cation, such analogues being described in U.S. Pat. No. 7,176,308, the entire disclosure of which is incorporated herein by reference in its entirety. Methylene blue is also known as basic blue 9. Other thio-heterocyclic cation sources include methylene green, i.e., basic green 5, Lauth's violet i.e., thionin. Oxidized forms of methylene blue may be employed as well, such as the thiazins methylene azure A, methylene azure B, and methylene azure C. In some embodiments, the thio-heterocyclic cation may be any member of the phenothiazin-3-ylidene-dimethylazanium structural class with any counter anion.

In certain embodiments, the thio-heterocyclic cation may be provided at substantially the lowest concentration sufficient to promote the desired degree of reduction of aggregates. In certain embodiments, the concentration of the thio-heterocyclic cation may be less than (on a weight per volume basis) 1%, 0.5%, 0.25%, 0.1%, 0.05%, 0.04%, 0.025%, or 0.001%. In certain embodiments the electropositive organic additive is provided in concentrations of 0.01-0.04% or 0.02-0.025%.

In certain embodiments, the disclosed methods may be practiced at pH levels chosen to avoid or limit precipitation of the desired protein while reducing the amount of aggregates in the sample. The pH level may be adjusted by conventional means and may be chosen in conjunction with the selection of the conductivity. In certain embodiments, the pH of the sample is between approximately 4 and approximately 9, between approximately 5 and approximately 8, or between approximately 6 and approximately 7.5.

In certain embodiments, the sample is additionally contacted with an antiviral agent beyond the thio-heterocyclic cation itself. In certain of such embodiments, the antiviral agent may be a non-multivalent organic cation, such as a benzalkonium chloride, chlorhexidine, ethacridine, or tri (n-butyl) phosphate. Such antiviral agents may be present in an amount less than approximately 1% (w/v), less than approximately 0.1% (w/v), or less than approximately 0.01% (w/v) or less than approximately 0.001%.

In certain embodiments, the method additionally includes the step of contacting the sample with a ureide in an amount sufficient for the ureide to be undissolved in the sample. The supernatant containing the desired protein may then be separated from the balance of the sample including precipitated contaminants. In certain of such embodiments the ureide is supplied prior to the step of contacting the sample with the electropositive organic additive, in others the ureide is supplied substantially simultaneously with the step of contacting the sample with the electropositive organic additive, and in yet others the ureide is supplied after the step of contacting the sample with the electropositive organic additive. In certain such embodiments, the ureide may be any of uric acid, hydantoin (imidazolidine-2,4-dione), allantoin (2,5-Dioxo-4-imidazolidinyl) urea, alcloxa, aldioxa, hemocane, ureidohydantoin, 5-ureidohydantoin), glyoxylureide, glyoxylic acid diureide, 2,5-dioxo-4-imidazolidinyl urea (allantoin), imidazolydinyl urea, diimidazolydinyl urea, and a purine. In certain embodiments the ureide is allantoin and in some such cases the allantoin is present in concentrations greater than 0.56% (w/v), 1%, 1.5%, 2%, or greater. In certain embodiments the ureide is uric acid and in some such cases the uric acid is present in concentrations greater than 0.0025% (w/v), 0.005%, 0.01%, 0.05%, 0.1%, 1% or greater.

In certain embodiments, methods may additionally include a step of contacting the sample with a ureide in an amount where the ureide is fully dissolved. In certain such embodiments, the soluble ureide may be urea, imidazolydinal urea, or another ureide. In certain embodiments the ureide is urea and in some such cases the urea is present in concentrations greater than 0.5 M, or greater than 1 M, or greater than 2 M, or greater than 4 M, or than 6M, or greater than 8 M. The ability to perform methods herein combining thio-heterocyclic cations with ureides, including methylene blue, is surprising, where avoidance of precipitation is a particular goal of the method. This result contrasts with known ethacridine precipitation methods. Highly soluble ureides such as urea have the general effect of increasing the solubility of many compounds, which is to say their presence opposes the formation of precipitates.

In certain embodiments, the utility of the disclosed methods may be enhanced by accelerating sedimentation of cell debris in cell culture harvests, and substantially reducing levels of DNA, endotoxin, and virus, when present. Experimental data indicates that the ability of some ureides to preferentially interact with aggregates, endotoxin, and virus contribute to these results, and that low levels of dissolved ureides may contribute to the higher antibody recovery in comparison to treatment with multivalent cations in the absence of ureides. Following treatment, solid materials may be removed by sedimentation or filtration, leaving the substantially aggregate-free protein in the supernatant.

In certain embodiments, the disclosed methods may be practiced with the additional step of contacting the sample with a soluble organic modulator such as a nonionic organic polymer, organic solvent, surfactant, or ureide. In certain of such embodiments the step of contacting the sample with the organic modulator occurs prior to the step of contacting the sample with the electropositive organic additive. In others, the step of contacting the sample with the organic modulator occurs substantially simultaneously with the step of contacting the sample with the electropositive organic additive. In yet others, the step of contacting the sample with the organic modulator occurs after the step of contacting the sample with the electropositive organic additive. In certain embodiments, the organic modulator is a nonionic organic polymer such as polyethylene glycol, polypropylene glycol and polybutylene glycol and in certain of such embodiments the nonionic organic polymer has an average molecular weight of approximately 1000 D or less, 500 D or less, 250 D or less, or 100 D or less. In certain embodiments, the organic modulator is an organic solvent such as ethylene glycol, propylene glycol, butylene glycol, dimethylsulfoxide, ethanol, or phenoxyethanol. In certain embodiments, the organic modulator is provided at a concentration of approximately 1% (w/v) or greater. In certain embodiments, the organic modulator is a surfactant such as Tween, triton, CHAPS, CHAPSO or octyl glucoside and in certain of such embodiments the surfactant is provided at a concentration of approximately 1% (w/v) or less, approximately 0.1% or less or approximately 0.02% (w/v) or less. In certain embodiments, the organic modulator is a ureide provided in a subsaturating amount and in certain of such embodiments the ureide is urea, hydantoin, or allantoin.

In certain embodiments, the disclosed method may be practiced with the aid of a kit designed to carry out the disclosed methods. Such kit may provide instructions and reagents useful for the practice of the disclosed methods such one or more of multivalent organic cations, ureides, organic modulators, antiviral agents, and reagents for the adjustment of conductivity. The kit may provide materials in amounts and concentrations adapted to the practice of the disclosed methods for use in the purification of proteins. Such kits may be adapted for use with certain proteins such as IgG or IgM antibodies and may be adapted to quantities suitable for certain scales of protein preparation and purification.

In certain embodiments, the disclosed methods may be followed by contact of the sample with solid materials with the intent of the solids having the effect of selectively removing the excess thio-heterocyclic cations or other sample components from the sample prior to additional processing. In one such example, a negatively charged solid such as used for conducting the technique of cation exchange chromatography might be included to scavenge excess thio-heterocyclic cations. In another such example, a hydrophobic solid such as used for conducting the technique of hydrophobic interaction chromatography might be employed. In another such example, a negatively charged hydrophobic chromatography solid might be employed. In another type of example, a solid bearing a positive charge might be used to scavenge DNA, or pH indicator dyes, or phospholipids, or other components from the sample.

In certain embodiments, the disclosed methods may be combined with conventional protein purification methods to achieve higher levels of purification or to remove other contaminants. For example, the disclosed methods may be practiced in preparation for conventional purification methods involving precipitation, chromatography, and liquid-liquid extraction methods. It is within the ability of a person of ordinary skill in the art to develop appropriate conditions for these methods and integrate them with the disclosed methods described herein to achieve the desired purification of a product.

In certain embodiments, operating conditions may be varied with respect to pH, and/or by the presence of chelating agents, organic polymers or solvents, surfactants, chaotropes, and various species of salts in order to modulate the degree to which aggregates are reduced and the desired protein remains in solution.

In some embodiments, there are provided methods of reducing the aggregate content in a protein preparation comprising a target protein, the method comprising: contacting the protein preparation with a thio-heterocyclic cation to form a mixture, contacting the mixture with at least one functionalized solid to remove excess thio-heterocyclic cations, and optionally contacting the mixture, simultaneously or sequentially, with at least one further functionalized solid to further reduce aggregate content of the protein preparation. In one such embodiment, solid particles functionalized to provide elevated hydrophobicity and negative charge may be included to scavenge excess thio-heterocyclic cations, at the same time that solid particles functionalized to provide a positive charge may be included to bind aggregates that contain an integrated DNA component. In one such embodiment, a solid functionalized to provide electropositivity may further include other chemical functionalities, such as hydrogen bonding, hydrophobicity, and/or metal affinity.

In some embodiments, the thio-heterocyclic cation is methylene blue.

In one or more of the preceding embodiments, the thio-heterocyclic cation is present in a concentration range selected from the group consisting of: (a) from about 0.001% to about 1%; (b) from about 0.01 to about 1%, and (c) from about 0.02 to about 0.03%, including any intermediate value or range of values.

In one or more of the preceding embodiments, allantoin is present in a concentration range selected from the group consisting of (a) from about 0.6 to about 50%; (b) from about 1 to about 10%; and (c) from about 1 to about 2%, including any intermediate value or range of values.

In one or more of the preceding embodiments, an operating conductivity is within a range selected from the group consisting of: (a) from about 0.1 to about 50 mS/cm; (b) from about 1 to about 30 mS/cm; and (c) from about 5 to about 15 mS/cm, including any intermediate value or range of values.

In one or more of the preceding embodiments, an operating pH is in a range selected from the group consisting of: (a) from about 4 to about 10; (b) from about 5 to about 9; from about 6 to about 8, and from about 6.5 to 7.5, including any intermediate value or range of values.

In one or more of the preceding embodiments, the mixture further comprises an antiviral agent other than the thio-heterocyclic cation, the antiviral agent selected from the group consisting of chlorhexidine, benzalkonium chloride, ethacridine, and tri(n-butyl)phosphate.

In some embodiments, the thio-heterocyclic cation may be used in combination with allantoin. Allantoin may improve the ability of methylene blue to accomplish aggregate reduction.

In one or more of the preceding embodiments, the mixture further comprises allantoin in a concentration ranging from one of the group consisting of (a) from about 0.6% to about 50%, (b) from about 0.1% to about 25%, (c) from about 0.8% to about 10%, (d) from about 0.9% to about 5%, and (e) from about 1% to about 2%, including any intermediate value or range of values.

In one or more of the preceding embodiments, a surface of the at least one functionalized solid provides a chemical interaction selected from the group consisting of: electrostatic interactions, hydrophobic interactions, hydrogen bonding, and metal affinity.

In one or more of the preceding embodiments, the at least one functionalized solid is particulate.

In one or more of the preceding, embodiments, the target protein comprises one selected from the group consisting of a recombinant protein, an antibody, a growth hormone, and a clotting factor.

In one or more of the preceding embodiments, the protein preparation is one selected from the group consisting of a cell-containing cell culture harvest, a substantially cell-free cell culture harvest, and a partially purified protein.

In some embodiments, there are provided kits for the convenient practice of the methods disclosed herein. Such kits may include instructions, reagents, and optionally any pre-packed equipment in the form of pre-packed chromatography devices or simple containers.

Terms are defined below so that the disclosed methods may be understood more readily. Additional definitions are set forth throughout the detailed description.

"Aggregate(s)" refers to an association of two or more molecules that is stable at physiological conditions and may remain stable over a wide range of pH and conductivity conditions. Aggregates frequently comprise at least one biomolecule such as a protein, nucleic acid, or lipid and another molecule or metal ion. The association may occur through any type or any combination of chemical interactions. Aggregates of antibodies may be classified into two categories: "Homoaggregates" refers to a stable association of two or more proteins of identical composition; "Heteroaggregates" refers to a stable association of one or more proteins of identical or different composition, optionally associated with one or more non-protein molecules. The non-protein component may consist of one more entities from the group consisting of a nucleotide, an endotoxin, a metal ion, a lipid, or a cell culture media component.

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')$_2$, Fv, scFv, Fd, dAb, Fc and other compositions, whether or not they retain antigen-binding function.

"Endotoxin" refers to a toxic heat-stable lipopolysaccharide substance present in the outer membrane of gram-negative bacteria that is released from the cell upon lysis.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the disclosed methods include but are not limited to polyethylene glycol (PEG), polypropylene glycol, and polyvinylpyrrolidone (PVP). PEG has a structural formula HO—(CH$_2$—CH$_2$—O)$_n$—H. Examples include, but are not limited to compositions with an average polymer molecular weight ranging from less than 100 to more than 1000 daltons.

"Thio-heterocyclic cation" refers to an organic cation comprising 3 rings in a coplanar arrangement, bearing at least one thiol group and at least one amino group, bearing at least one positive charge where the positive charge may reside with the thiol or with an amino group. One example is methylene blue.

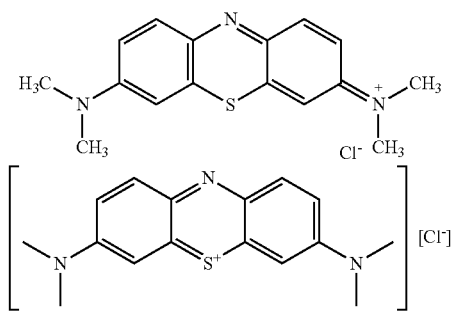

"Organic solvent" refers to naturally occurring or synthetic organic compound existing in a liquid state. Examples suitable to practice the disclosed methods include but are not limited to ethylene glycol, propylene glycol, dimethyl-sulfoxide, ethanol, and phenoxyethanol.

"Organic polymer" refers to a naturally occurring synthetic polymer of an organic monomer. Examples include but are not limited to polyethylene glycol, polypropylene glycol, dextran, or cellulose, among others.

"Polynucleotide" refers to a biopolymer composed of multiple nucleotide monomers covalently bonded in a chain. DNA (deoxyribonucleic acid) and RNA (ribonucleic acid) are examples of polynucleotides.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Undissolved ureide" refers to a solution containing an amount of ureide in excess of its maximum solubility under the conditions prevailing in a particular protein preparation. In certain embodiments, the disclosed methods provides a sample with a ureide present in an amount greater than such ureide's solubility in such sample under the conditions for such sample such that some fraction of such ureides is present in an undissolved form in the sample.

"Surfactant" includes "surface active agents" such as a class of organic molecules that generally comprise a hydrophobic portion and a hydrophilic portion, causing them to be referred to as amphiphilic. At sufficient concentrations in aqueous solutions, surfactants may self-associate into clusters with the hydrophobic portions concentrated at the center to minimize contact with water, and the hydrophilic portions radiating outwards to maximize contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing certain embodiments of the disclosed methods include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3,3-tetramethylbutyl)-phenyl ether), and zwitterionic surfactants such as CHAPS (3-[(3-Cholamidopropyl)dimethylammonio]-1-propanesulfonate), CHAPSO (3-[(3-cholamidopropyl) dimethylammonio]-2-hydroxy-1-propanesulfonate), and octyl glucoside (e.g., (2R,3S,4S,5R,6R)-2-(hydroxymethyl)-6-octoxyoxane-3,4,5-triol).

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

In preparation for using the disclosed methods according to certain embodiments, it will be necessary to select a thio-heterocyclic cation. Experimental data reveal methylene blue to be desirable for its effectivity in reducing aggregates, in addition its ability to inactivate virus. Its use as an anti-malarial drug and therapeutic agent for treatment of methemoglobinenia highlights its compatibility with in vivo human use, and it is listed in the U.S. Pharmacopeia.

In the course of evaluation of thio-heterocyclic cations for use in certain embodiments, the conditions for application may be investigated as follows. The use of thio-heterocyclic cations potentially imposes some restrictions on the conditions that may be used to practice the method in certain embodiments. For example, it may be desirable to employ conditions that substantially prevent strong interactions between the thio-heterocyclic cations and the protein of interest. A simple method to obtain an approximation of such conditions is to apply the protein of interest to an anion exchanger and elute it in a salt gradient. A salt concentration just above the threshold at which the protein elutes roughly identifies the minimum conductivity at which the method may be effectively practiced. This concentration will be influenced by pH, which may be modeled by the same means. Given that the method is applied to a cell culture supernatant, an IgG antibody may not require the addition of salt or modification of pH to avoid significant losses. IgM antibodies may require the addition of salt, even to conductivity values approaching 30 mS/cm (about 2 times higher than physiological). In certain embodiments involving the use of undissolved ureides and electropositive organic additives, IgG applications may be conducted at lower than physiological conductivity, potentially including values of 1 mS/cm or less, in which case substantial amounts of host proteins may be removed in conjunction with dissociating aggregates. Such applications may require that the concentration of the thio-heterocyclic cations be increased to compensate for the amount that is los through binding to host proteins. Lower operating conductivities in such circumstances may also enhance removal of DNA, endotoxin, and virus. In certain embodiments, the disclosed methods will generally support antibody recovery greater than 95%, and usually 98-99%. Conductivity and pH conditions of the sample should typically be established before adding either the ureide or the thio-heterocyclic cations.

In certain embodiments, one effective means of evaluating conditions for clarified cell culture supernatants containing IgG monoclonal, antibodies is to cover a range of 0.01 to 0.1% thio-heterocyclic cations, and conductivities ranging from half-physiological to 2 times physiological. The ranges may be extended further if results indicate it may be helpful to do so, or narrowed and evaluated at finer increments.

In certain embodiments, a convenient starting point for developing a purification procedure according to the disclosed methods for clarified cell culture supernatants is to use 0.025% methylene blue.

In certain embodiments, it may be advantageous to begin by dispersing an organic modulator in the protein preparation before adding the electropositive organic additive, since that practice may improve antibody recovery. Long incubation before addition of the electropositive organic additive appears to be unnecessary; 15 minutes or less is adequate, although there appears to be no disadvantage to longer incubation. Experimental data generally indicate that addition of allantoin in a supersaturating amount of about 1% increases the recovery of IgG.

In certain embodiments, it is recommended that the thio-heterocyclic cations cation be dissolved, for example in water or buffer, prior to its addition to the sample, to facilitate their rapid distribution throughout the protein preparation. Care should be taken to avoid persistent local excesses, for example by gradually infusing the dissolved thio-heterocyclic cations into a well-mixing suspension. Incubation time should be at least 15 minutes, or about 30 minutes, but need not be greater than about 60 minutes.

The method may generally be practiced at ambient temperature but may be conducted at higher or lower temperatures, for example ranging from 4° to 37° C. Experimental data indicate that the temperature does not substantially alter the obtained results, which will leave the stability requirements of the protein itself as a governing factor in selection of operating temperature.

In certain embodiments, the thio-heterocyclic cations is dissolved or dispersed, for example in water or buffer, and the pH adjusted prior to its addition to the sample. This is because certain preparations of thio-heterocyclic cations, such as free-base forms, are alkaline and have the potential to substantial altering the experimental conditions in an unintended manner.

In certain embodiments involving the use of both superstaturated ureides and thio-heterocyclic cations, it may generally be advantageous to begin by dispersing the ureide in the protein preparation before adding the thio-heterocyclic cations, since experience with the ureide allantoin indicates that this practice may improve antibody recovery. Long incubation before addition of the electropositive organic additive appears to be unnecessary; 15 minutes or less is adequate, although there appears to be no disadvantage to longer incubation.

Multiple options exist for monitoring the aggregate dissociation or removal achieved by the method, whether during method development or manufacturing. The simplest is to conduct analytical size exclusion chromatography on a column with suitable selectivity and monitor at a UV wavelength of 280 nm. This may reveal HMW (high molecular weight) aggregates, since they usually include hydrodynamic dimension that reasonably conform to multiples of the size of the non-aggregated product. Hetero-aggregates are commonly overlooked by this method since their hydrodynamic dimensions may be only modestly greater than those of the non-aggregated product. In such cases, the heteromorphic composition of the aggregate may be revealed by calculating the ratio of UV absorbance at 254 nm to absorbance at 280 nm, then comparing that value against the absorbance ratio for purified protein that is believed to be totally free of associated contaminants. Hetero-aggregates containing DNA, for example, will be revealed by an elevated ratio of 254/280. If the chromatograph offers the capability, methylene blue content may be monitored simultaneously at 655 nm. This may be helpful for documenting the removal of methylene blue through the subsequent purification process. Multiple wavelength monitoring may also be used in conjunction with other chromatography methods. Methylene blue may alternatively be monitored by reversed phase high performance liquid chromatography.

In certain embodiments, the disclosed methods may be integrated with treatment to remove the thio-heterocyclic cations and potentially other components of the sample prior to subsequent purification. Such treatments may include exposure of the sample to solids bearing chemical moieties that are complementary in their nature to the characteristics of the thio-heterocyclic cations with the goal that they sequester the thio-heterocyclic cations from the remainder of the sample. Since thio-heterocyclic cations are understood to be positively charged and hydrophobic, it follows that negatively charged surfaces, including hydrophobic negatively charged surfaces, should be especially useful for sequestering excess thio-heterocyclic cations. Solids of other surface composition may be included to sequester other components of the sample.

In certain embodiments, the disclosed methods may be integrated with one or more purification methods, including but not limited to protein A and other forms of biological affinity chromatography, anion exchange chromatography, cation exchange chromatography, hydrophobic interaction chromatography, immobilized metal affinity chromatography, hydroxyapatite or other mixed mode chromatography, and/or non-chromatographic methods such as precipitation and liquid-liquid extraction. It is within the purview of a person of ordinary skill in the art to develop appropriate conditions for the various methods and integrate them with the disclosed methods herein to achieve the necessary purification of a particular antibody.

EXAMPLES

Example 1

Independent effects of methylene blue versus ethacridine. Cell culture harvest containing and IgG1 monoclonal antibody at a concentration of about 2 g/L was clarified by centrifugation and microfiltration. Aggregate content was 21% and host protein content was 371,459 parts per million of IgG. In a control series of experiments, different aliquots of clarified harvest were mixed with 0.01%, 0.02%, or 0.04% ethacridine and incubated stirring for 2 hours. In another series, methylene blue was added to separate aliquots at the same concentrations. Solid particles synthesized from a negatively charged polymer bearing hydrophobic butyl groups (MacroPrep tbutyl, Bio-Rad Laboratories) were added to a level of 5% vol/vol, and incubated mixing for 16 hours. Solids were removed by centrifugation. Aggregate content and host protein content were reduced in both series, but more by methylene blue. For ethacridine, aggregates were reduced to 17%, versus 16% with methylene blue, with very little difference with respect to the concentration of ethacridine or methylene blue. For ethacridine, host protein was reduced to 327,621, 315,180, and 307,014 ppm across the range from 0.01 to 0.04%. For methylene blue, the corresponding values were 259,357, 240,059, 221,810 ppm, showing an average 24% better performance by methylene blue. IgG recovery was 91% in both groups. Another distinction was observed between ethacridine-treated and methylene blue-treated harvest: in samples treated with ethacridine, a portion of free antibody light chain appeared to dimerize spontaneously. This was not observed with methylene blue, and the phenomenon was not investigated further, however, the presence of the sulfur atom on methylene blue has been postulated as playing a potential role.

Example 2

Methylene blue mixed with allantoin. Cell culture harvest containing and IgG1 monoclonal antibody at a concentration of about 2 g/L was clarified by centrifugation and microfiltration. Aggregate content was 6.8% and host protein content was 406,239 ppm of IgG. Allantoin was added in an amount of 1% w/v. Methylene blue was added in an amount of 0.02% and the mixture incubated for 2 hours. Positively charged particles (Bio-Works TREN high) were added in an amount of 2.5% v/v, and negatively charged particles (Bio-Rad Macroprep high S) were, added in the same proportion and incubated mixing for 16 hours. Solids were removed by centrifugation and microfiltration. Aggregates were reduced to 3.3% and host protein was reduced to 143,362 ppm, with an IgG of 91%. The mixture was passed through a pair of depth filters (PB1 and PC1, Sartorius). Aggregates were reduced to 2.1%. Host proteins were reduced to 43,360 ppm, with an IgG recovery of 86%.

Example 3

Aggregate reduction of an IgG containing cell culture harvest. An IgG cell-culture harvest containing about 21% aggregates was treated by titrating the pH to 8.0, adding allantoin to a final concentration of 1% w/v, followed by addition of methylene blue in an amount of 0.025%. The mixture was incubated stirring at room temperature for 1 hour. A 4:1 mixture of Bio-Works TREN-high and Macroprep t-Butyl particles were equilibrated to 50 mM tris, 100 mM NaCl, pH 8.0, the particles were settled and a volume of mixed particles amounting to 5% of the volume of the IgG preparation was added to the preparation. The mixture was incubated stirring for 4 hours and the solids were removed by centrifugation. A sample removed for analysis revealed that aggregates were reduced from the original 21% to 2.1%. DNA was reduced by more than 99% (AccuBlue, Biotium) and host proteins were reduced by 81% (host protein ELISA, Cygnus). The mixture was passed through a pair of depth filters (PB1 and PC1, Sartorius). Aggregates were further reduced to less than 0.5%, and host proteins were reduced by a total of 91% compared to the original harvest.

Example 4

Aggregate reduction of an IgM-containing cell culture harvest. An IgG cell culture harvest containing about 23% aggregates was treated by addition of NaCl in an amount to produce a final conductivity of 20 mS/cm, followed by addition of allantoin in a final proportion of 1%, followed by addition of methylene blue in an amount of 0.025%. The mixture was incubated stirring at room temperature for 2 hours. A 1:1:1:1 mixture of Macroprep High S, Macroprep High Q, Macroprep t-Butyl, and Chelex 100 (Bio-Rad), was equilibrated to 50 mM sodium phosphate, 200 mM NaCl, pH 7.2, the particles were settled and a volume of mixed particles amounting to 5% of the volume of the IgM preparation was added to the preparation. The preparation was incubated stirring for 4 hours, and the solids were removed by centrifugation followed by membrane filtration through a 0.22 micron membrane. Aggregate content was reduced from the original 23% to less than 1%. DNA was reduced by more than 99%, and host cell protein contamination was reduced by 47%.

It will be understood by the person of ordinary skill in the art how to scale up or scale down the results from experiments such as those described in the above examples, to whatever volume required to meet their particular requirements.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present disclosed methods.

Many modifications and variations of the disclosed methods may be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the disclosed methods being indicated by the following claims.

The invention claimed is:

1. A method of reducing an aggregate content in a protein preparation comprising a target protein, the method comprising:
   (a) contacting the protein preparation with methylene blue to form a mixture, wherein the methylene blue is present in the mixture at a concentration range from about 0.001% to about 1% (weight/volume);
   (b) contacting the mixture with at least a first functionalized solid comprising (i) negatively charged particles comprising hydrophobic groups, or (ii) a combination of negatively charged cation exchange particles and positively charged particles comprising Tris(2-aminoethyl)amine (TREN); and
   (c) removing the at least first functionalized solid from the mixture, thereby providing a protein preparation substantially free of aggregates, wherein the protein preparation substantially free of aggregates comprises the target protein.

2. The method of claim 1, wherein the protein preparation substantially free of aggregates comprises an aggregate content of 3.3% or less.

3. The method of claim 1, comprising contacting the mixture, simultaneously or sequentially, with a second functionalized solid.

4. The method of claim 3, wherein the at least second functionalized solid comprises positive charged particles.

5. The method claim 1, wherein the methylene blue is present in a concentration range of from about 0.01 to about 1%, or from about 0.02 to about 0.03%.

6. The method of claim 1, comprising, prior to (c), contacting the protein preparation or the mixture with allantoin in a concentration range selected from the group consisting of: (a) from about 0.6 to about 50%, (b) from about 1 to about 10%, and (c) from about 1 to about 2%.

7. The method of claim 1, wherein a conductivity of the protein preparation or the mixture is within a range selected from the group consisting of: (a) from about 0.1 to about 50 mS/cm, (b) from about 1 to about 30 mS/cm, and (c) from about 5 to about 15 mS/cm.

8. The method of claim 1, wherein an operating pH of the protein preparation or the mixture is in a range selected from the group consisting of: (a) from about 4 to about 10, (b) from about 5 to about 9, (c) from about 6 to about 8, and (d) from about 6.5 to about 7.5.

9. The method of claim 1, wherein the mixture, prior to (c), comprises an antiviral agent selected from the group consisting of chlorhexidine, benzalkonium chloride, ethacridine, and tri(n-butyl)phosphate.

10. The method of claim 1, wherein the mixture, prior to (c), comprises allantoin at a concentration ranging from one of the group consisting of (a) from about 0.6% to about 50%, (b) from about 0.7% to about 25%, (c) from about 0.8% to about 10%, (d) from about 0.9% to about 5%, and (e) from about 1% to about 2%.

11. The method of claim 1, wherein the target protein comprises one selected from the group consisting of a recombinant protein, an antibody, a growth hormone, and a clotting factor.

12. The method of claim 1, wherein the protein preparation is one selected from the group consisting of a cell-containing cell culture harvest, a substantially cell-free cell culture harvest, and a partially purified protein.

13. The method of claim 1, wherein the at least first functionalized solid comprises a combination of negatively charged cation exchange particles and positively charged particles comprising Tris(2-aminoethyl)amine (TREN).

14. The method of claim 1, wherein the at least first functionalized solid comprises negatively charged particles comprising hydrophobic butyl groups.

15. The method of claim 1, comprising, after the removing, filtering the mixture.

16. A method of reducing an aggregate content in a protein preparation comprising a recombinant protein, the method comprising:
   (a) contacting the protein preparation with methylene blue to a concentration of about 0.001% to about 1% (weight/volume), allantoin to a concentration of about 0.6 to about 50% (weight/volume), and a first functionalized solid comprising negatively charged hydrophobic particles;
   (b) removing the at least first functionalized solid from the mixture, thereby providing a protein preparation substantially free of aggregates, wherein the protein preparation substantially free of aggregates comprises the recombinant protein.

* * * * *